(12) United States Patent
Huttner et al.

(10) Patent No.: US 12,402,974 B1
(45) Date of Patent: Sep. 2, 2025

(54) LIGHTED SURGICAL INSTRUMENT

(71) Applicant: Bionix, LLC, Maumee, OH (US)

(72) Inventors: James Huttner, Sylvania, OH (US); Mackenzie Eickhoff Vocke, Napoleon, OH (US)

(73) Assignee: Bionix, LLC, Maumee, OH (US)

( * ) Notice: Subject to any disclaimer, the term of this patent is extended or adjusted under 35 U.S.C. 154(b) by 0 days.

(21) Appl. No.: 17/841,835

(22) Filed: Jun. 16, 2022

Related U.S. Application Data

(60) Provisional application No. 63/213,270, filed on Jun. 22, 2021.

(51) Int. Cl.
| | |
|---|---|
| *A61B 90/30* | (2016.01) |
| *A61B 17/16* | (2006.01) |
| *A61F 11/00* | (2022.01) |
| *A61F 11/20* | (2022.01) |
| A61B 17/00 | (2006.01) |
| A61B 17/3207 | (2006.01) |
| A61B 17/50 | (2006.01) |

(52) U.S. Cl.
CPC .......... *A61B 90/30* (2016.02); *A61B 17/1679* (2013.01); *A61F 11/006* (2013.01); *A61F 11/20* (2022.01); *A61B 2017/00738* (2013.01); *A61B 17/320708* (2013.01); *A61B 17/50* (2013.01); *A61B 2090/309* (2016.02)

(58) Field of Classification Search
CPC .......... A61F 11/20; A61F 11/006; A61B 2017/00738; A61B 17/320708; A61B 1/0623; A61B 1/063; A61B 1/07; A61B 1/0676; A61B 1/0684; A61B 2090/309; A61B 90/30; A61B 17/1679; A61B 2090/306; A61B 17/50
See application file for complete search history.

(56) References Cited

U.S. PATENT DOCUMENTS

| | | | | | |
|---|---|---|---|---|---|
| 4,043,322 | A | * | 8/1977 | Robinson | A61B 1/303 |
| | | | | | 606/160 |
| 4,572,180 | A | * | 2/1986 | Deenadayalu | A61F 11/006 |
| | | | | | 600/249 |
| 5,234,452 | A | * | 8/1993 | Wang-On | A61B 17/50 |
| | | | | | 606/160 |
| 5,586,989 | A | * | 12/1996 | Bray, Jr. | A61B 17/320708 |
| | | | | | 606/160 |
| 6,398,793 | B1 | * | 6/2002 | McGuire | A61B 17/320708 |
| | | | | | 606/160 |
| D771,815 | S | * | 11/2016 | Huttner | D24/151 |

(Continued)

*Primary Examiner* — Julianna N Harvey
(74) *Attorney, Agent, or Firm* — Marshall & Melhorn, LLC

(57) ABSTRACT

A lighted surgical instrument has an instrument body defining a proximal portion, a distal portion, and a mid-portion extending between the proximal portion and the distal portion. The proximal portion includes a base adapted to receive a light source and a linear section defining a first axis, while the distal portion has a linear section defining a second axis and terminating in a functional tip, with the second axis of the distal portion is parallel to but offset from the first axis of the proximal portion. The linear section of the proximal portion may have a cross-sectional shape of a Reuleaux triangle. The instrument body is capable of functioning as a light pipe, such that light introduced into the base of the proximal portion will be transmitted to the functional tip of the instrument by internal reflection.

14 Claims, 3 Drawing Sheets

(56) References Cited

U.S. PATENT DOCUMENTS

| | | | | |
|---|---|---|---|---|
| 10,092,168 B1* | 10/2018 | Huttner | ............... | A61B 17/062 |
| 11,166,740 B1* | 11/2021 | Schumaier | ............. | A61B 90/35 |
| 2008/0092337 A1* | 4/2008 | Gross | ..................... | B25G 1/102 |
| | | | | 81/489 |
| 2010/0042122 A1* | 2/2010 | Shaw, Jr. | .............. | A61F 11/006 |
| | | | | 606/162 |
| 2013/0190647 A1* | 7/2013 | Pahuja | .................. | A61F 11/006 |
| | | | | 606/162 |
| 2016/0184046 A1* | 6/2016 | Blain | ................ | A61B 17/1659 |
| | | | | 600/249 |

* cited by examiner

LIGHTED SURGICAL INSTRUMENT

BACKGROUND OF THE INVENTION

Ear curettage is a commonly performed procedure, usually done for the purposes of removing occluding wax (cerumen) and/or foreign bodies from the ear canal. As an example, approximately 10 million visits to a physician are made annually for complaints of ear pain in children. In a large majority of these patients, occluding cerumen must be removed first to enable the physician to properly examine the ear canal.

Ear curettage has typically been a "blind" procedure. The physician first notes the presence and placement of the occluding cerumen through direct examination of the ear canal using an otoscope. Then, using a non-lighted ear curette, the physician blindly scrapes the ear canal in an attempt to remove the obstruction. This can be a painful process, and one that is not always successful in removing the occluding wax.

An improvement to this procedure occurred with the introduction of the lighted ear curette. This device used a clear plastic curette as a light pipe to conduct light from an attached light source into the ear canal. Using a lighted ear curette the physician could now illuminate the ear canal to enable visualization of the occluding cerumen and allow its removal under direct observation.

The lighted ear curette still has deficiencies, however. The lighted ear curette is designed as having a single linear axis, resulting in a straight light pipe. This means that light entering the rearward end of the curette travels by total internal reflection in an axial direction until it emits from the forward tip of the curette. It can be seen in FIG. 1 that the light-path axis of the curette and the visual (eye line) axis are not the same. Depending on the user and how they hold the curette, the visual axis may be 15 degrees or greater above the light-path axis when viewed in the frontal plane. This can cause problems when trying to visualize cerumen in a long, narrow tube such as the ear canal, as the hand and fingers may obstruct the view. This problem is accentuated when trying to visualize the narrower ear canal of children. Although light may illuminate the distal reaches of the ear canal, the angular deviation between the visual axis and light-path axis will limit the depth to which adequate visualization can occur.

A second deficiency with the current lighted ear curette is that there is no region designed for natural finger grip placement. As curettage is often a delicate procedure performed on very young children, it is important that the user have a solid, natural grasp on the curette.

SUMMARY OF THE INVENTION

The invention is a lighted surgical instrument has an instrument body defining a proximal portion, a distal portion, and a mid-portion extending between the proximal portion and the distal portion. The proximal portion includes a base adapted to receive a light source and a linear section defining a first axis, while the distal portion has a linear section defining a second axis and terminating in a functional tip, with the second axis of the distal portion is parallel to but offset from the first axis of the proximal portion. The linear section of the proximal portion may have a cross-sectional shape of a Reuleaux triangle. The instrument body is capable of functioning as a light pipe, such that light introduced into the base of the proximal portion will be transmitted to the functional tip of the instrument by internal reflection.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The invention is an improved, lighted surgical instrument 10, especially an improved lighted ear curette. In certain embodiments, the invention addresses deficiencies in the conventional lighted ear curette by introducing a lighted curette wherein the visual axis and light-path axis are identical, providing full illumination and enhanced visualization of obstructions in the ear canal, and/or the invention addresses other deficiencies in the conventional lighted ear curette by adding a unique triangular shape to the proximal portion of the curette for an enhanced, ergonomic grip.

Figure 1:
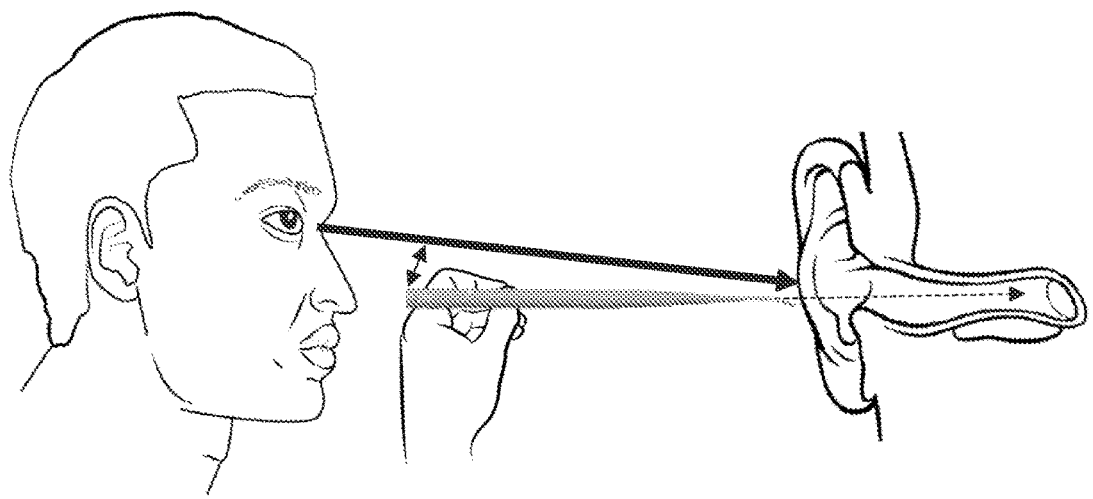
FIG. 1 is a somewhat schematic view of a prior art ear curette in use, depicting the visual path of the user vs the axis of the prior art ear curette.
Figure 2:
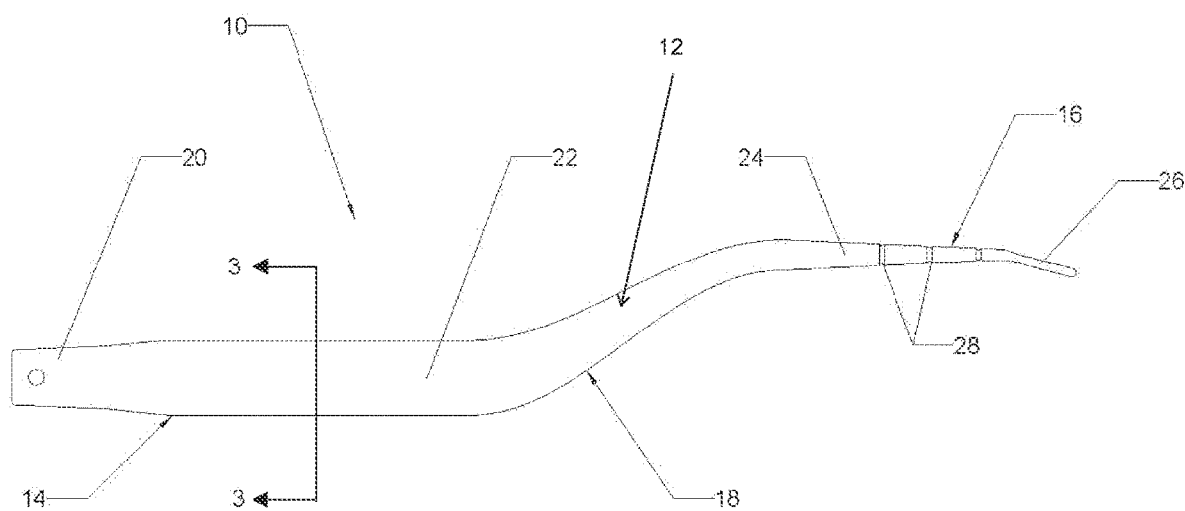
FIG. 2 is a side view of a preferred embodiment of a lighted ear curette in accordance with the invention.

The lighted surgical instrument of the invention includes an instrument body 12. The instrument body 12 is capable of functioning as a light pipe, such that light introduced into one end of the body will be transmitted therethrough and exit the other end of the body. In the embodiment of the invention illustrated in FIG. 2, the instrument body 12 is a curette body having an off-set design defining three portions of the curette. The instrument body 12 defines a proximal portion 14, a distal portion 16, and a mid-portion 18 extending between the proximal portion 14 and the distal portion 16.

Figure 3:
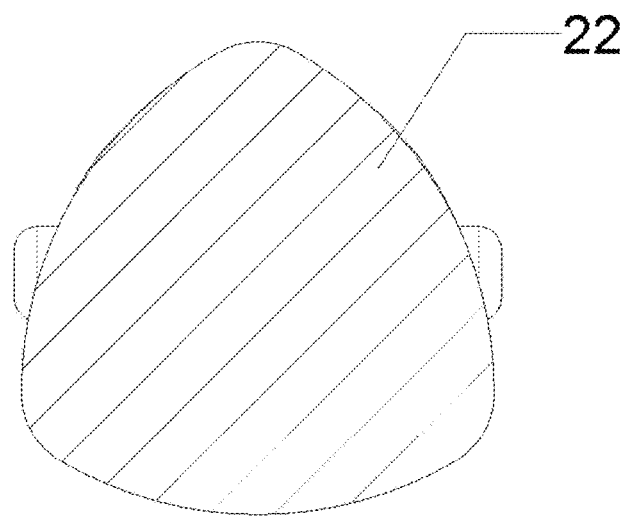
FIG. 3 is an enlarged, cross-sectional view through lines 3-3 of FIG. 2.

The proximal portion 14 of the body 12 includes a rearward base 20 adapted to attach to and receive a light source, and a linear section 22 defining a first axis and acting as a finger-grip portion for the user of the instrument body 12. A preferred cross-sectional shape of the linear section 22 is shown in FIG. 3 This portion of the curette has a roughly triangular shape in what is known as a "Reuleaux triangle." A Reuleaux triangle is a shape having a boundary that is a curve of constant width. The Reuleaux triangular cross-sectional shape of the linear section 22 of the proximal portion 12 provides a natural, ergonomic finger grip for the device, while still retaining the light pipe properties of the instrument body 12. In a further preferred aspect, the Reuleaux triangular cross-sectional shape extends the entire length from the base 20 to the start of the mid-portion 18, allowing proper finger placement by users of varying hand sizes, large and small.

The distal portion 16 of the instrument body 12 has a linear section 24 defining a second axis and terminating in a functional tip 26. As a result of the angles between the proximal portion 14 and the mid-portion 18, and then again between the mid-portion 18 and the distal portion 16, the second axis defined by the distal portion 16 is parallel to but offset from the first axis defined by the proximal portion 14. Thus, the noted configuration of the portions of the instrument body 12 raises the visual axis of the distal portion 16/functional tip 26 above the linear axis of the proximal portion 14.

In certain preferred embodiments, at least a portion of the linear section 24 of the distal portion 16 tapers towards the functional tip 26. In further embodiments, at least a portion of the linear section 24 of the distal portion 16 is provided with a circular cross-sectional shape.

The working or functional tip 26 of the instrument body 12 may have any of multiple suitable configurations. In the illustrated embodiment, the lighted surgical instrument 10 is a lighted ear curette and the functional tip 26 is configured as a loop. In certain preferred embodiments, the linear section 24 of the distal portion 16 is provided with a plurality of visible index marks 28 to designate depth or position of the functional tip, for example within the ear canal of a patient.

Figure 4:
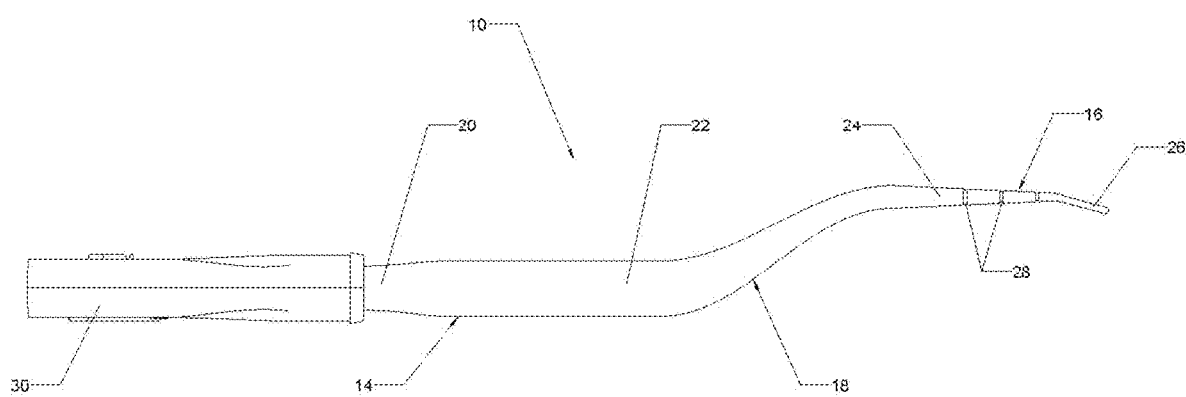
FIG. 4 is a side view of the ear curette of FIG. 2 with light source attached to the distal end thereof.

As shown in FIG. 4, a light source 30 may be attached to the base 20 of the instrument body 12. Preferably, the light source 30 is an LED light contained within a housing that is selectively attachable to the base 20, such as by a threaded connection, a bayonet-type connection, or the like.

In a preferred embodiment, the entire instrument/curette body 12 is formed of unitary molded construction and is comprised of a clear, light-conducting plastic. A transparent polycarbonate is especially preferred. Preferably, the instrument body exhibits less than 5% haze, and 95% or better clarity. When light is introduced into the rearward face of the base 20 of the proximal portion 14 of the body 12, the light is transmitted via total internal reflection to the functional tip 26 of the curette, where it is emitted. Preferably, the light introduced into the base 20 will be transmitted to the functional tip 26 of the instrument essentially in its entirety by internal reflection.

Figure 5:
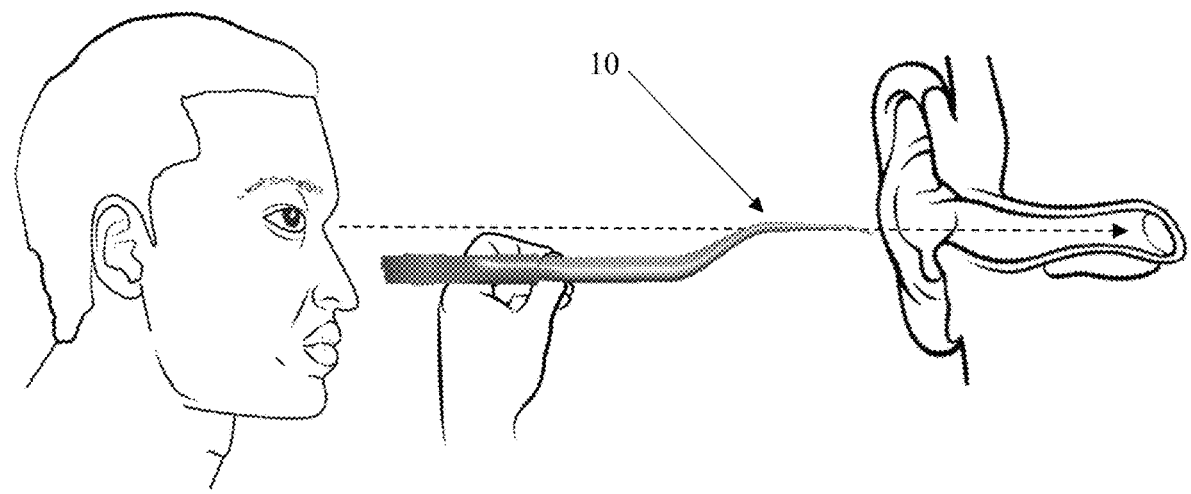
FIG. 5 is a somewhat schematic view of the ear curette of FIG. 2 in use, depicting the visual path of the user vs the axis of the ear curette.

FIG. 5 illustrates an embodiment of the lighted curette of the invention in use. As shown in the drawing, the visual axis (defined as a line running from the user's eye line to the distal working tip of the curette) is roughly identical with the linear axis of the distal portion of the curette. This allows the user to visualize obstructions deeper into the ear canal of the patient than previously possible using an ear curette with only a single, straight light-pipe.

In accordance with the provisions of the patent statutes, the invention has been described in what is considered to represent its preferred embodiments. However, it should be noted that the invention could be practiced otherwise than as specifically illustrated and described without departing from its spirit or scope.

What is claimed is:

1. A lighted surgical instrument comprising an instrument body defining a proximal portion, a distal portion, and a mid-portion extending between the proximal portion and the distal portion;
   wherein the proximal portion is comprised of a base adapted to receive a light source and a linear section defining a first axis;
   wherein the distal portion is comprised of a linear section defining a second axis and terminating in a functional tip, and wherein at least a portion of the linear section of the distal portion is both solid in cross section and tapers towards the functional tip;
   wherein the second axis of the distal portion is parallel to but offset from the first axis of the proximal portion;
   wherein the second axis of the distal portion is co-linear with the visual axis of curettage, as defined by an imaginary line connecting the eye line of a user with the linear axis of an ear canal of a patient; and
   wherein the instrument body is capable of functioning as a light pipe, such that light introduced into the base of the proximal portion will be transmitted to the functional tip of the instrument by internal reflection.

2. The lighted surgical instrument of claim 1, wherein at least a portion of the linear section of the proximal portion has a cross-sectional shape of a Reuleaux triangle.

3. The lighted surgical instrument of claim 2, wherein the linear section of the proximal portion has a cross-sectional shape of a Reuleaux triangle along its entire length from the base to the mid-portion of the instrument body.

4. The lighted surgical instrument of claim 1, wherein the instrument body is formed of a single unitary piece of molded plastic.

5. The lighted surgical instrument of claim 1, wherein the instrument body is comprised of a transparent polycarbonate.

6. The lighted surgical instrument of claim 1, further comprising a light source attached to the base of the instrument body and configured to introduce light into the base of the proximal portion of the instrument body so that the light is transmitted through the instrument body and is emitted from the functional tip.

7. The lighted surgical instrument of claim 6, wherein the light source is an LED light source.

8. The lighted surgical instrument of claim 1 wherein at least a portion of the linear section of the distal portion has a circular cross-sectional shape.

9. The lighted surgical instrument of claim 1, wherein the instrument body exhibits less than 5% haze.

10. The lighted surgical instrument of claim 1, wherein the instrument body exhibits 95% or better clarity.

11. The lighted surgical instrument of claim 1, wherein the functional tip is comprised of a loop for ear curettage.

12. The lighted surgical instrument of claim 1, wherein the linear section of the distal portion includes a plurality of visible index marks to designate depth or position of the functional tip.

13. A lighted surgical instrument comprising an instrument body formed of a single unitary piece of molded plastic and defining a proximal portion, a distal portion, and a mid-portion extending between the proximal portion and the distal portion;
   wherein the proximal portion is comprised of a base adapted to receive a light source and a linear section defining a first axis, with at least a portion of the linear section of the proximal portion having a cross-sectional shape of a Reuleaux triangle;
   wherein the distal portion is comprised of a linear section defining a second axis and terminating in a functional tip, and wherein at least a portion of the linear section of the distal portion is both solid in cross section and tapers towards the functional tip;

wherein the second axis of the distal portion is parallel to but offset from the first axis of the proximal portion;

wherein the second axis of the distal portion is co-linear with the visual axis of curettage, as defined by an imaginary line connecting the eye line of a user with the linear axis of an ear canal of a patient; and wherein the instrument body is capable of functioning as a light pipe, such that light introduced into the base of the proximal portion will be transmitted to the functional tip of the instrument by internal reflection.

14. A lighted surgical instrument comprising an instrument body defining a proximal portion, a distal portion, and a mid-portion extending between the proximal portion and the distal portion;

wherein the proximal portion is comprised of a base adapted to receive a light source and a linear section defining a first axis;

wherein the distal portion is comprised of a linear section defining a second axis and terminating in a functional tip, and wherein at least a portion of the linear section of the distal portion is both circular in cross section and tapers towards the functional tip;

wherein the second axis of the distal portion is parallel to but offset from the first axis of the proximal portion;

wherein the second axis of the distal portion is co-linear with the visual axis of curettage, as defined by an imaginary line connecting the eye line of a user with the Page 6 linear axis of an ear canal of a patient; and wherein the instrument body is capable of functioning as a light pipe, such that light introduced into the base of the proximal portion will be transmitted to the functional tip of the instrument by internal reflection.

* * * * *